United States Patent
Bawden et al.

(10) Patent No.: US 9,128,086 B2
(45) Date of Patent: Sep. 8, 2015

(54) DETECTION OF HISTONE MODIFICATION IN CELL-FREE NUCLEOSOMES

(75) Inventors: Lindsay Jane Bawden, Abingdon (GB); Elizabeth Ann Bone, Abingdon (GB); Alan Hastings Drummond, Abingdon (GB); Lindsey Ann Needham, Abingdon (GB)

(73) Assignee: SINGAPORE VOLITION PTE. LIMITED, Singapore (SG)

( * ) Notice: Subject to any disclaimer, the term of this patent is extended or adjusted under 35 U.S.C. 154(b) by 1734 days.

(21) Appl. No.: 10/568,691

(22) PCT Filed: Aug. 18, 2004

(86) PCT No.: PCT/GB2004/003564
§ 371 (c)(1),
(2), (4) Date: Aug. 30, 2006

(87) PCT Pub. No.: WO2005/019826
PCT Pub. Date: Mar. 3, 2005

(65) Prior Publication Data
US 2007/0160989 A1    Jul. 12, 2007

(30) Foreign Application Priority Data
Aug. 18, 2003    (GB) .................................. 0319376.0

(51) Int. Cl.
| | | |
|---|---|---|
| *G01N 1/00* | (2006.01) |
| *G01N 33/00* | (2006.01) |
| *G01N 33/48* | (2006.01) |
| *G01N 33/50* | (2006.01) |
| *G01N 33/53* | (2006.01) |
| *G01N 33/558* | (2006.01) |
| *G01N 33/564* | (2006.01) |
| *G01N 33/574* | (2006.01) |
| *G01N 33/68* | (2006.01) |

(52) U.S. Cl.
CPC ........ *G01N 33/564* (2013.01); *G01N 33/57488* (2013.01); *G01N 33/6875* (2013.01)

(58) Field of Classification Search
CPC ......... G01N 1/00; G01N 33/00; G01N 33/48; G01N 33/50; G01N 33/53; G01N 33/558; G01N 33/564; G01N 33/574; G01N 33/5784; G01N 33/57488; G01N 33/6863; G01N 33/6875
See application file for complete search history.

(56) References Cited

U.S. PATENT DOCUMENTS

| | | | |
|---|---|---|---|
| 2005/0069931 A1* | 3/2005 | Allis et al. ........................ 435/6 |
| 2006/0073517 A1* | 4/2006 | Allis et al. ..................... 435/7.1 |
| 2008/0248039 A1* | 10/2008 | Kurdistani et al. ........ 424/138.1 |

FOREIGN PATENT DOCUMENTS

| | | | |
|---|---|---|---|
| EP | 1 316 619 A | 6/2003 |
| WO | 99/47924 A | 9/1999 |
| WO | 03/014142 A | 2/2003 |
| WO | 03/070894 A | 8/2003 |

OTHER PUBLICATIONS

Ausio et al. Histone variants and histone modifications: A structural perspective. Biochemistry and Cell Biology (79): 693-708, 2001.*
Luger et al. Crystal structure of the nucleosome core particle at 2.8 Å resolution. Nature (389): 251-260 (Sep. 18, 1997).*
Feng et al. Methylation of H3-lysine 79 is mediated by a new family of HMTases without a SET domain. Current Biology 12:1052-1058, Jun. 25, 2002.*
International Search Report of PCT/GB2004/003564, mailed Jan. 13, 2005.

* cited by examiner

*Primary Examiner* — Alana Harris Dent
(74) *Attorney, Agent, or Firm* — Nixon & Vanderhye P.C.

(57) ABSTRACT

This invention relates to the diagnosis of disease conditions, such as cancer and autoimmune disease, by the analysis of cell-free nucleosomes in samples from individuals. Methods of the invention may include contacting cell-free nucleosomes from a biological fluid sample obtained from the individual with an antibody that binds specifically with a modified histone protein. Binding of the antibody to the nucleosomes is indicative that the individual has the disease condition.

20 Claims, 3 Drawing Sheets

```
                       SEQUENCE LISTING

<160> NUMBER OF SEQ ID NOS: 16

<210> SEQ ID NO 1
<211> LENGTH: 8
<212> TYPE: PRT
<213> ORGANISM: Homo sapiens
<220> FEATURE:
<223> OTHER INFORMATION: Example of peptide which may be used to
      generate modified histone specific antibodies: H3 lys 4 (Me)
<220> FEATURE:
<221> NAME/KEY: MOD_RES
<222> LOCATION: (4)..(4)
<223> OTHER INFORMATION: METHYLATION

<400> SEQUENCE: 1

Ala Arg Thr Lys Gln Thr Ala Arg
1               5

<210> SEQ ID NO 2
<211> LENGTH: 5
<212> TYPE: PRT
<213> ORGANISM: Homo sapiens
<220> FEATURE:
<223> OTHER INFORMATION: Example of peptide which may be used to
      generate modified histone specific antibodies: H4 arg 3 (Me)
<220> FEATURE:
<221> NAME/KEY: MOD_RES
<222> LOCATION: (3)..(3)
<223> OTHER INFORMATION: METHYLATION

<400> SEQUENCE: 2

Ser Gly Arg Gly Lys
1               5

<210> SEQ ID NO 3
<211> LENGTH: 5
```

```
<212> TYPE: PRT
<213> ORGANISM: Homo sapiens
<220> FEATURE:
<223> OTHER INFORMATION: Example of peptide which may be used to
      generate modified histone specific antibodies: H4 lys 5 (Ac)
<220> FEATURE:
<221> NAME/KEY: MOD_RES
<222> LOCATION: (5)..(5)
<223> OTHER INFORMATION: ACETYLATION

<400> SEQUENCE: 3

Ser Gly Arg Gly Lys
1               5

<210> SEQ ID NO 4
<211> LENGTH: 5
<212> TYPE: PRT
<213> ORGANISM: Homo sapiens
<220> FEATURE:
<223> OTHER INFORMATION: Example of peptide which may be used to
      generate modified histone specific antibodies: H4 arg 3 (Me)/lys
      5 (Ac)
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (5)..(5)
<223> OTHER INFORMATION: ACETYLATION

<400> SEQUENCE: 4

Ser Gly Arg Gly Lys
1               5

<210> SEQ ID NO 5
<211> LENGTH: 5
<212> TYPE: PRT
<213> ORGANISM: Homo sapiens
<220> FEATURE:
<223> OTHER INFORMATION: Example of peptide which may be used to
      generate modified histone specific antibodies: H4 Ser 2(phos)/Arg
      3 (me)/Lys 5 (Ac)
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (5)..(5)
<223> OTHER INFORMATION: ACETYLATION

<400> SEQUENCE: 5

Ser Gly Arg Gly Lys
1               5

<210> SEQ ID NO 6
<211> LENGTH: 9
<212> TYPE: PRT
<213> ORGANISM: Homo sapiens
<220> FEATURE:
<223> OTHER INFORMATION: Example of peptide which may be used to
      generate modified histone specific antibodies: H3 lys 9 (Me)
<220> FEATURE:
<221> NAME/KEY: MOD_RES
<222> LOCATION: (5)..(5)
<223> OTHER INFORMATION: METHYLATION

<400> SEQUENCE: 6
```

```
Gln Thr Ala Arg Lys Ser Thr Gly Val
1               5
```

```
<210> SEQ ID NO 7
<211> LENGTH: 11
<212> TYPE: PRT
<213> ORGANISM: Homo sapiens
<220> FEATURE:
<223> OTHER INFORMATION: Example of peptide which may be used to
      generate modified histone specific antibodies: H2B ser 14 (Phos)
<220> FEATURE:
<221> NAME/KEY: MOD_RES
<222> LOCATION: (9)..(9)
<223> OTHER INFORMATION: PHOSPHORYLATION

<400> SEQUENCE: 7

Ser Ala Pro Ala Pro Lys Lys Gly Ser Lys Lys
1               5                   10
```

```
<210> SEQ ID NO 8
<211> LENGTH: 10
<212> TYPE: PRT
<213> ORGANISM: Homo sapiens
<220> FEATURE:
<223> OTHER INFORMATION: Example of peptide which may be used to
      generate modified histone specific antibodies: H3 lys 27 (Me)
<220> FEATURE:
<221> NAME/KEY: MOD_RES
<222> LOCATION: (4)..(4)
<223> OTHER INFORMATION: METHYLATION

<400> SEQUENCE: 8

Ala Ala Arg Lys Ser Ala Pro Val Cys Gly
1               5                   10
```

```
<210> SEQ ID NO 9
<211> LENGTH: 11
<212> TYPE: PRT
<213> ORGANISM: Homo sapiens
<220> FEATURE:
<223> OTHER INFORMATION: Example of peptide which may be used to
      generate modified histone specific antibodies: H3 lys 36 (Me)
<220> FEATURE:
<221> NAME/KEY: MOD_RES
<222> LOCATION: (5)..(5)
<223> OTHER INFORMATION: METHYLATION

<400> SEQUENCE: 9

Ser Gly Gly Val Lys Lys Pro His Lys Cys Gly
1               5                   10
```

```
<210> SEQ ID NO 10
<211> LENGTH: 10
<212> TYPE: PRT
<213> ORGANISM: Homo sapiens
<220> FEATURE:
<223> OTHER INFORMATION: Example of peptide which may be used to
      generate modified histone specific antibodies: H4 lys 20 (Me)
<220> FEATURE:
<221> NAME/KEY: MOD_RES
<222> LOCATION: (4)..(4)
<223> OTHER INFORMATION: METHYLATION

<400> SEQUENCE: 10

Arg His Arg Lys Ile Leu Arg Asp Cys Gly
1               5                   10
```

```
<210> SEQ ID NO 11
<211> LENGTH: 135
```

<212> TYPE: PRT
<213> ORGANISM: Homo sapiens

<400> SEQUENCE: 11

```
Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135
```

<210> SEQ ID NO 12
<211> LENGTH: 102
<212> TYPE: PRT
<213> ORGANISM: Homo sapiens

<400> SEQUENCE: 12

```
Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala Arg Arg Gly Gly Val Lys Arg Ile Ser Gly
        35                  40                  45

Leu Ile Tyr Glu Glu Thr Arg Gly Val Leu Lys Val Phe Leu Glu Asn
    50                  55                  60

Val Ile Arg Asp Ala Val Thr Tyr Thr Glu His Ala Lys Arg Lys Thr
65                  70                  75                  80

Val Thr Ala Met Asp Val Val Tyr Ala Leu Lys Arg Gln Gly Arg Thr
                85                  90                  95

Leu Tyr Gly Phe Gly Gly
            100
```

<210> SEQ ID NO 13
<211> LENGTH: 129
<212> TYPE: PRT
<213> ORGANISM: Homo sapiens

<400> SEQUENCE: 13

```
Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr Ala Glu Arg Val Gly Ala Gly Ala Pro
        35                  40                  45

Val Tyr Leu Ala Ala Val Leu Glu Tyr Leu Thr Ala Glu Ile Leu Glu
```

```
                 50                  55                  60
Leu Ala Gly Asn Ala Ala Arg Asp Asn Lys Lys Thr Arg Ile Ile Pro
 65                  70                  75                  80

Arg His Leu Gln Leu Ala Ile Arg Asn Asp Glu Glu Leu Asn Lys Leu
                 85                  90                  95

Leu Gly Lys Val Thr Ile Ala Gln Gly Val Leu Pro Asn Ile Gln
                100                 105                 110

Ala Val Leu Leu Pro Lys Lys Thr Glu Ser His His Lys Ala Lys Gly
                115                 120                 125

Lys

<210> SEQ ID NO 14
<211> LENGTH: 125
<212> TYPE: PRT
<213> ORGANISM: Homo sapiens

<400> SEQUENCE: 14

Pro Glu Pro Ser Lys Ser Ala Pro Ala Pro Lys Lys Gly Ser Lys Lys
 1               5                  10                  15

Ala Ile Thr Lys Ala Gln Lys Lys Asp Gly Lys Lys Arg Lys Arg Ser
                20                  25                  30

Arg Lys Glu Ser Tyr Ser Ile Tyr Val Tyr Lys Val Leu Lys Gln Val
                35                  40                  45

His Pro Asp Thr Gly Ile Ser Ser Lys Ala Met Gly Ile Met Asn Ser
                50                  55                  60

Phe Val Asn Asp Ile Phe Glu Arg Ile Ala Gly Glu Ala Ser Arg Leu
 65                  70                  75                  80

Ala His Tyr Asn Lys Arg Ser Thr Ile Thr Ser Arg Glu Ile Gln Thr
                85                  90                  95

Ala Val Arg Leu Leu Leu Pro Gly Glu Leu Ala Lys His Ala Val Ser
                100                 105                 110

Glu Gly Thr Lys Ala Val Thr Lys Tyr Thr Ser Ser Lys
                115                 120                 125

<210> SEQ ID NO 15
<211> LENGTH: 142
<212> TYPE: PRT
<213> ORGANISM: Homo sapiens

<400> SEQUENCE: 15

Ser Gly Arg Gly Lys Thr Gly Gly Lys Ala Arg Ala Lys Ala Lys Ser
 1               5                  10                  15

Arg Ser Ser Arg Ala Gly Leu Gln Phe Pro Val Gly Arg Val His Arg
                20                  25                  30

Leu Leu Arg Lys Gly His Tyr Ala Glu Arg Val Gly Ala Gly Ala Pro
                35                  40                  45

Val Tyr Leu Ala Ala Val Leu Glu Tyr Leu Thr Ala Glu Ile Leu Glu
                50                  55                  60

Leu Ala Gly Asn Ala Ala Arg Asp Asn Lys Lys Thr Arg Ile Ile Pro
 65                  70                  75                  80

Arg His Leu Gln Leu Ala Ile Arg Asn Asp Glu Glu Leu Asn Lys Leu
                85                  90                  95

Leu Gly Gly Val Thr Ile Ala Gln Gly Gly Val Leu Pro Asn Ile Gln
                100                 105                 110

Ala Val Leu Leu Pro Lys Lys Thr Ser Ala Thr Val Gly Pro Lys Ala
                115                 120                 125
```

```
Pro Ser Gly Gly Lys Lys Ala Thr Gln Ala Ser Gln Glu Tyr
    130                 135                 140
```

<210> SEQ ID NO 16
<211> LENGTH: 135
<212> TYPE: PRT
<213> ORGANISM: Homo sapiens

<400> SEQUENCE: 16

```
Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
            85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
            115                 120                 125

Arg Ile Arg Gly Glu Arg Ala
    130                 135
```

DETECTION OF HISTONE MODIFICATION IN CELL-FREE NUCLEOSOMES

This application is the US national phase of international application PCT/GB2004/003564, filed 18 Aug. 2004, which designated the U.S. and claims priority of GB 0319376.0, filed 18 Aug. 2003, the entire contents of each of which are hereby incorporated by reference.

This invention relates to the diagnosis of disease conditions, such as cancer and autoimmune disease, by the analysis of cell-free nucleosomes in samples from individuals, in particular the analysis of cell-free nucleosomes containing histone modifications.

In eukaryotes, DNA is complexed with proteins to form nucleosomes, the basic sub-unit of chromatin. Nucleosomes consist of approximately 150 DNA base pairs wrapped around a histone core, which is a protein complex involving the four histones H4, H3, H2B and H2A. The amino-terminal tails of these proteins are among the most evolutionary conserved proteins known. These tails are post-translationally modified by the addition of a range of chemical groups including methyl, acetyl and phosphoryl. These chemical modifications, or marks, play a key role in determining chromatin structure and hence access to the cells genomic DNA (Wu J and Grunstein M (2000) Trends Biochem. Sci. 25, 619-623; Berger S L (2001) Oncogene 20, 3007-3013). It has also been shown that the marks are involved in the control mechanism for a wide range of cellular processes. For example, in general, deacetylation of marks and certain methylation marks are associated with gene silencing (Hu J F and Hoffman A R (2001) Methods Mol Biol 181, 285-296; Rice J C and Allis C D (2001) Curr Opin Cell Biol 13, 263-273; Carrozza M J et al (2003) Trends Genet 19, 321-329; Nephew K P and Huang T H (2003) Cancer Lett 190, 125-133) and phosphoryl marks with apoptosis (Enomoto R et al (2001) Mol Cell Biol Res Commun 4, 276-281; Ajiro K (2000) J Biol Chem 275, 439-443; Talasz H, et al (2002) Cell Death Differ 9, 27-39; Rogakou E P et al (2000) J Biol Chem 275, 9390-9395) and mitosis (Crosio et al (2002) Mol Cell Biol 22 874-885; Goto et al (2002) Genes Cells 7, 11-17; Hans and Dimitrov (2001) Oncogene 20, 3021-3027; Preuss et al (2003) Nucl Acids Res 31, 878-885). Nucleosomes marked in a specific manner can be isolated from cells by using specific antibodies, and the DNA component analysed (for example, Clayton et al (2000) EMBO J 19, 3714-3726; Li et al (2001) Mol Cell Biol 21, 8213-8224; Osano and Ono (2003) Eur J Biochem 270, 2532-2539; Kondo and Issa (2003) J Biol Chem (2003) 278(30): 27658-62).

Patients suffering from conditions, such as cancer and autoimmune disease, have nucleosomes circulating in the blood resulting from increased apoptosis (Holdenrieder et al (2001) Int J Cancer 95, 114-120; Trejo-Becerril et al (2003) Int J Cancer 104, 663-668; Kuroi et al 1999 Breast Cancer 6, 361-364; Kuroi et al (2001) Int j Oncology 19, 143-148; Amoura et al (1997) Arth Rheum 40, 2217-2225; Williams et al (2001) J Rheumatol 28, 81-94). Measurement of the levels of cell-free nucleosomes has been proposed as a means of diagnosing diseases associated with apoptosis (Holdenrieder et al (1999) Anticancer Res. 19, 2721-2724). However, the presence of cell-free nucleosomes with specific marks was not assessed.

The present invention relates to methods for detecting nucleosomes containing modified histones in samples from patients, in particular methods that involve antibody-antigen interactions.

Various aspects of the invention relate to the use antibodies which specifically bind to modified histones to detect nucleosomes in samples which comprise modified histones.

One aspect of the invention provides a method of assessing a disease condition in an individual comprising;
  contacting said nucleosomes from a biological fluid sample obtained from the individual with an antibody which binds specifically with a modified histone protein, wherein binding of said antibody to said nucleosomes is indicative that the individual has a disease condition.

A disease condition in the individual may be assessed by determining one or more of: the presence of one or more histone modifications in the sample, an increase in the number of cell-free nucleosomes containing modified histones in the sample relative to normal levels, an alteration in the ratio of one or more particular histone modifications relative to another histone modifications in the sample and a threshold number of nucleosomes in the sample which comprise a histone modification.

After the biological fluid sample has been contacted with the antibody under conditions suitable to allow specific binding of the antibody to its target antigen, nucleosomes comprising the modified histone may be identified and, optionally, isolated using standard techniques.

A biological fluid suitable for use in accordance with the present methods may include sera, plasma, lymph, blood, blood fractions, urine, synovial fluid, spinal fluid, saliva, and mucous. Blood, serum or plasma are preferred.

Nucleosomes may be concentrated from the biological fluid sample before contact with the antibody. Nucleosomes may be concentrated from the sample of biological fluid by any convenient concentration method, including, for example:
  centrifugal filtration such as centrifugal filtration units with an appropriate molecular weight cut-off membrane e.g. Millipore's Centricon® or Amicon® units,
  acid precipitation (Yoshida, M et al, (1990), J Biol Chem 265, 17174-17179).
  immunoprecipitation using conventional methods, for example, by incubating the sample with an anti-nucleosome antibody or a histone mark-specific antibody, and then immunopurifying the antibody/antigen complex using a spin column packed with an immunoaffinity matrix. The captured nucleosomes would then be eluted and analysed.
  Separation based on charge, for example, binding to polyK coated solid supports (Williams R C et al, (2001) J Rheumatol 28, 81-94).
  Separation based on biotinylation. Histones can be biotinylated by biotinidase (Hymes J et al (1995), Biochem Mol Med 56, 76-83; Stanley J S et al, (2001) Eur J Biochem 268, 5424-5429.

In some embodiments, nucleosomes may be concentrated by a method other than collection on a poly K or streptavidin-coated support.

A histone mark may be a post-translational chemical change to one or more histone amino acid residues, for example addition/removal of a chemical group or isomerisation of an amino acid residue.

An antibody specific for a modified histone is specific for a unique epitope formed by post-translational modification of a core histone, for example histone H2A, H2B, H3, H4 (Luger, K. et al (1997) Nature 389, 251-260) or a modification or variant thereof (see for example (Ausio J (2001) Biochem Cell Bio 79, 693). Known sequences of histones are described in the NHGRI/NCBI histone sequence database which is accessible on-line.

A modification may be in the central region of a histone or in the flexible N-terminal or C-terminal tail.

Post-translational modification may include acetylation, methylation, which may be mono-, di- or tri-methylation, phosphorylation, ribosylation, citrullination, ubiquitination, hydroxylation, glycosylation, nitrosylation, glutamination and/or isomerisation (Ausio J (2001) Biochem Cell Bio 79, 693).

A lysine residue which is methylated may be mono-, di- or tri-methylated. An arginine residue which is methylated may be symmetrically or asymmetrically dimethylated, or monomethylated.

An histone amino acid residue having a modification may be any Ser, Lys, Arg, His, Glu, Pro or Thr residue within the histone amino acid sequence.

For example, a lysine residue within the core histone sequence may be mono-, di- or tri-methylated, acetylated or ubiquitinated, an arginine residue within the core histone sequence may be monomethylated, symmetrically or asymmetrically dimethylated or converted to citrulline, a serine or threonine residue within the core histone sequence may be phosphorylated and/or a proline residue within the core sequence may be isomerised.

The notation used to describe a particular histone modification indicates which histone has been modified, the particular amino acid(s) that have been modified and the type of modification that has occurred. For example H3 Lys 9(Me) denotes the methylation of histone H3 at lysine 9.

Examples of modifications include modifications shown in table 1.

A histone mark which produces a cellular effect may consist of one modification to a histone or may consist of two or more histone modifications. In other words, a single mark, which may for example be associated with silencing or activation, may consist of a combination of separate modifications to different residues within a histone sequence.

For example, a modified histone may comprise a mark which is associated with gene silencing, such as H3 Lys 9(Me) H3 Lys 27(Me), H3 Lys 36(Me), H3 Lys 79(Me) and H4 Lys 20(Me) or a mark which is associated with gene activation, such as H3 Lys 4(Me) H3 Lys 9(Ac), H3 Lys 14(Ac) and H3 Lys 23(Ac)

Antibodies which are specific for histone marks that are associated with active gene sequences (euchromatin) or inactive gene sequences (heterochromatin) may be used, for example, to detect inappropriate gene expression which is indicative of a disease state. Screening the population of cell-free nucleosomes present in a sample from an individual may reveal the inactivation of a tumour suppression gene or alternatively, the activation of an oncogene.

A 'modified nucleosome' is a nucleosome which comprises a histone comprising one or more modifications as described above.

An antibody which specifically binds to an antigen such as a modified histone or nucleosome may not show any significant binding to molecules other than the antigen. An antibody may specifically bind to a particular epitope which is carried by a number of antigens, in which case the antibody will be able to bind to the various antigens carrying the epitope.

In some embodiments, a disease condition may be assessed by determining the presence of two or more histone modifications in cell-free nucleosomes in the sample. In particular, the presence of a histone mark consisting of more than one modification may be determined by determining the presence of the two or more separate modifications. Two or more histone modifications in a sample may be characterised by contacting the sample with an antibody that specifically binds to two or more histone modifications or alternatively, contacting the sample with two or more antibodies, each antibody specifically binding to a different histone modification.

Another aspect of the invention comprises a method of assessing histone modification in cell-free nucleosomes in a biological fluid sample comprising;
  contacting a biological fluid sample with an antibody which binds specifically to a histone comprising a modification; and,
  determining the binding of said antibody to nucleosomes in said sample,
  the binding of said antibody being indicative of the presence of modified histone in nucleosomes in the blood of said individual.

An antibody may specifically bind to a histone modification described above, for example a modification shown in Table 1, or a combination of such modifications.

In some preferred embodiments, an antibody may bind specifically to a histone comprising a modification shown in Table 2 or a combination of such modifications.

In some embodiments, the biological fluid sample may be contacted with a further antibody which binds specifically to histone comprising a different modification from the first antibody. A range of antibodies may be employed to detect the presence of a range of histone modifications.

Cell-free nucleosomes in fluid samples from patients may be used to assess disease conditions associated with cell death, in particular cancer and/or autoimmune disease. For example, the presence of cancer cells in an individual may generate a higher level of cell free nucleosomes in the blood as a result of the increased apoptosis of the cancer cells. An antibody directed against marks associated with apoptosis, such as H2B Ser 14(P), may be used to selectively isolate nucleosomes that have been released from apoptotic neoplastic cells.

Another aspect of the invention provides a method of assessing a disease condition in an individual comprising;
  contacting biological fluid sample obtained from an individual with an antibody which binds specifically to a modified histone,
  determining the binding of said antibody to nucleosomes in said sample,
  the binding of said antibody to nucleosomes in said sample being indicative that said individual has a disease condition.

A modified histone may, for example, have a modification selected from the group consisting of H2B Ser 14 (Phos), H3 lys 9(Me), H3 lys 27(Me) and H3 Ser 10 (Phos). In some embodiments, the modified histone is not H2B Ser 14(Phos).

Diseases associated with modified, cell-free nucleosomes include, but are not limited to, pre-malignant and malignant neoplasms and tumours, (e.g., histocytoma, glioma, astrocyoma, osteoma), cancers (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, autoimmune diseases (e.g. systemic lupus erythematosus) and proliferative disorders (e.g. psoriasis, bone diseases, fibroproliferative disorders of connective tissue, cataracts and atherosclerosis).

A pre-malignant or malignant condition may occur in any cell-type, including but not limited to, lung, colon, breast, ovarian, prostate, liver, pancreas, brain, and skin.

An antibody that specifically binds to a modified histone may be generated using techniques which are conventional in the art. Methods of producing antibodies include immunising a mammal (e.g. mouse, rat, rabbit, horse, goat, sheep or monkey) with a modified histone or a peptide fragment of the histone which comprises the modification or mark. Peptide fragments with particular modifications can be designed from known histone sequences and produced by routine synthesis methods. Antibodies may be obtained from immunised animals using any of a variety of techniques known in the art, and screened, preferably using binding of antibody to antigen of interest. For instance, Western blotting techniques or immunoprecipitation may be used (Armitage et al., (1992) Nature 357, 80-82).

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies suitable for use in accordance with the present methods are also available from commercial suppliers.

The binding of an antibody may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

Radioimmunoassay (RIA) is another possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample, the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colour or cause changes in electrical properties, for example. They may be excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. The mode of determining binding is not a feature of the present invention and those skilled in the art are able to choose a suitable method according to their preference and general knowledge.

The signals generated by individual antibody-reporter conjugates may be used to derive quantifiable absolute or relative data of the relevant antibody binding in samples (normal and test).

Methods of the invention may be carried out in any convenient format. Immunological assays are well-known in the art and many suitable formats are available, for example ELISA, Western blotting, or Biacore®, (Biacore, Upsala, Sweden). In some preferred embodiments, a sandwich assay format may be employed. A sandwich assay employs a capture antibody and a detection antibody to detect the presence of antigen in a sample. The capture antibody may, for example, bind specifically to a nucleosome and the detection antibody to a histone with a particular modification, or vice versa.

Another aspect of the invention provides a method of assessing histone modification in cell-free nucleosomes in a biological fluid sample from an individual comprising;

contacting a biological fluid sample from said individual with a first antibody; and, determining binding of said first antibody to a nucleosome comprising a histone modification using a second antibody, wherein one of said first or second antibodies binds to a nucleosome and the other of said first or second antibodies binds specifically to a modified histone.

In some embodiments, the first antibody binds to nucleosomes and the second antibody binds specifically to the modified histone. A method of assessing histone modification in nucleosomes in a biological fluid sample from an individual may thus comprise;

contacting a biological fluid sample from said individual with a first antibody which binds to nucleosomes; and, determining the presence of a modified histone in a nucleosome bound by said first antibody using a second antibody which binds specifically to a modified histone.

Antibodies which bind specifically to modified histones are described in more detail above. An antibody which binds to a nucleosome may bind to any epitope commonly found on any unmodified component of the nucleosomes, including histone and non-sequence specific DNA epitopes. In some embodiments, an antibody may bind to both the histone and DNA components of the nucleosome. An antibody may bind specifically to one or more nucleosome components.

Suitable anti-nucleosome antibodies include the antibody known as clone 11E6 (available from BD PharMingen) which interacts with the (H2A-H2B)-DNA sub-nucleosomal complex (Jovelin F et al (1998) Eur J Immunol 28, 3411).

In other embodiments, the second antibody binds to nucleosomes and the first antibody binds specifically to the modified histone. A method of assessing histone modification in nucleosomes in a biological fluid sample from an individual may thus comprise;

contacting a biological fluid sample from said individual with a first antibody which binds specifically to a modified histone, determining the binding of said first antibody to a nucleosome comprising a modified histone using a second antibody which binds to a nucleosome.

One of said first and second antibodies may be immobilised and the binding of the other antibody may be detected. Preferably, the first antibody is immobilised. An antibody may be immobilised, for example, by attachment to an insoluble support. The support may be in particulate or solid form and may include a plate, a test tube, beads, a ball, a filter or a membrane. An antibody may, for example, be fixed to an insoluble support that is suitable for use in affinity chromatography. Methods for fixing antibodies to insoluble supports are known to those skilled in the art. An antibody may be immobilised, for example, to isolate cell-free nucleosomes from the biological fluid sample.

The non-immobilised antibody may comprise a detectable label as described above. For example, the antibody may be labeled with a fluorophore such as FITC or rhodamine, a radioisotope, or a non-isotopic labeling reagent such as biotin or digoxigenin; antibodies containing biotin may be detected using "detection reagents" such as avidin conjugated to any desirable label such as a fluorochrome.

In some embodiments, the non-immobilised antibody may be detected using a third antibody which binds to said non-immobilised antibody. A suitable third antibody is labelled and is binds specifically to the first or second antibody. The third antibody may comprise a detectable label.

In some embodiments, a blocking reagent may be used to block or absorb interfering endogenous components, such as antibodies or proteins. For example, samples may be depleted of endogenous antibodies by, for example, application to a spin column packed with an immunoaffinity matrix to remove immunoglobulin. Alternatively, the potential interference by heterophilic antibodies could be minimised by the use of a blocking reagents. Suitable blocking reagents are available commercially, for example, HBR from Scantibodies Ltd (Santee, Calif., US)). Excess albumin in samples may conveniently be depleted by using an albumin affinity spin column (Montages™ Albumin Deplete kit, Millipore).

Antibodies specific for modified histones may be used to detect any abnormal modifications that would indicate a disease state. Alternatively, the nucleic acid sequences associated with modified nucleosomes may be analyzed using standard techniques to assess a disease condition or susceptibility to a disease condition.

Methods as described herein may be used to isolate and/or identity nucleic acid sequences associated with a particular mark. These nucleic acid sequences may be associated with a disease condition. Identifying the DNA associated with modified nucleosomes may also be useful in monitoring the progress of a therapeutic treatment, for example, monitoring positive and/or adverse effects resulting from treatment.

Methods of the invention may comprise isolating a nucleosome comprising a modified histone. Nucleosomes comprising modified histones may be isolated by immunoprecipitation using a modified histone-specific antibody or a nucleosome specific antibody as described herein. Alternatively, nucleosomes may be isolated by binding to an immobilised antibody, as described above.

Once the nucleosomes have been isolated from the sample, the DNA associated with the nucleosomes can be recovered using standard techniques. For example, DNA may be immobilised onto filters, column matrices, or magnetic beads. Numerous commercial kits, such as the Qiagen QIAamp kit (Quiagen, Crawley, UK) may be used. Briefly, the sample may be placed in a microcentrifuge tube and combined with Proteinase K, mixed, and allowed to incubate to lyse the cells. Ethanol is then added and the lysate is transferred to a QIAamp spin column from which DNA is eluted after several washings. Optionally, the isolated DNA may be amplified through PCR or other amplification techniques. The sequence of the nucleosome-associated DNA may be obtained, for example to identify the polypeptide encoded by the DNA. Nucleosome associated DNA may be associated with a particular histone mark or modification. For example, depending on the binding specificity of the antibody used to initially isolate the nucleosomes from the sample, genes may be identified that are associated with activation or silencing marks.

Any of analytical procedures known to those skilled in the art may be used to identify the DNA sequences associated with isolated nucleosomes. DNA sequences may, for example, be identified by direct microsequencing of the purified DNA. Alternatively, the purified DNA may be first amplified using PCR technology or other amplifying technique before further analysis of the DNA.

In some embodiments, the DNA associated with the isolated nucleosomes may be identified by contacting the purified DNA with known nucleic acid sequences under conditions suitable for hybridisation of complementary sequences, wherein hybridisation of the purified DNA to its complement identifies the purified DNA sequence; and determining hybridisation. For example, Southern Blot analysis may be conducted in which either the known DNA sequences or the purified DNA serves as the labelled probe, and the unlabeled sequences are immobilized on a solid surface. Formation of nucleic acid duplexes is then detected. The nucleosome-associated DNA can then be identified from the sequence(s) to which it hybridises.

Nucleic acid probes can be labelled with a detectable marker using standard techniques known to those skilled in the art. For example the nucleic acid probes can be labelled with a fluorophore, a radioisotope, or a non-isotopic labelling reagent such as biotin or digoxigenin.

Known nucleic acid sequences, for example, sequences from various genes of interest, may be immobilized on a solid surface, as described above. Preferably, the sequences are immobilized in the form of a microarray, in which each known sequence is assigned a position on a solid surface. Preferably, the microarray comprises a plurality of DNA molecules, each having a different known sequence. The purified nucleosome DNA may be labelled and then placed in contact with a microarray of known sequences under conditions suitable for the hybridisation of complementary sequences. After a predetermined length of time the unbound and non-specifically bound material may be washed from the microarray and the array I screened for detectable signals. A signal generated at a specific position on the solid surface by hybridisation of a purified nucleosome DNA sequence to its complement, identifies the purified nucleosome DNA sequence.

Microarrays allow miniaturisation of assays, e.g. making use of binding agents (such as nucleic acid sequences) immobilised in small, discrete locations (microspots) and/or as arrays on solid supports or on diagnostic chips. These approaches can be particularly valuable as they can provide great sensitivity (particularly through the use of fluorescent labelled reagents), require only very small amounts of biological sample from individuals being tested and allow a variety of separate assays to be carried out simultaneously. This latter advantage can be useful as it provides an assay for a number of different sequences to be carried out using a single sample. Examples of techniques enabling this miniaturised technology are provided in WO84/01031, WO88/1058, WO89/01157, WO93/8472, WO95/18376/WO95/18377, WO95/24649 and EP-A-0373203, the subject matter of which are herein incorporated by reference.

The principles of microarray hybridisation are described in Yershov, G. et al (1996) Proc Natl Acad Sci USA 93 4913-4918, Cheung V. G. et al (1999) Nature Genetics 21 15-19, and Schena, M. (1999) DNA Microarrays "a practical approach", ISBN, 0-19-963777-6, Oxford press, editor B. D. Hames. In brief, the DNA microarray may be generated using oligonucleotides that have been selected to hybridise with the specific target polymorphism. These oligonucleotides may be applied by a robot onto a predetermined location of a glass slide, e.g. at predetermined X, Y Cartesian coordinates, and immobilised. The sample RNA or DNA (e.g. fluorescently labelled RNA or DNA) is introduced on to the DNA microarray and a hybridisation reaction conducted so that sample RNA or DNA binds to complementary sequences of oligonucleotides in a sequence-specific manner, and allow unbound material to be washed away. Sequences can thus be identified by their ability to bind to complementary oligonucleotides on the array and produce a signal. The absence of a fluorescent signal for a specific oligonucleotide probe indicates that the sequence of the sample DNA or RNA is not present on the micoarray. Of course, the method is not limited to the use of fluorescence labelling but may use other suitable labels known in the art. Fluorescence at each coordinate can be read using a suitable automated detector, in order to correlate each fluorescence signal with a particular oligonucleotide.

Hybridisation of nucleosome associated DNA from said individual may be compared with the hybridisation of nucleosome associated DNA from other individuals. For example, hybridisation patterns from a patient with a proliferative disorder may be compared with patterns from a healthy individual to identify genes whose chromatin is differentially marked (for example, activated or inactivated) in the proliferative disorder. For example, a tumour suppressor gene may be associated with a silencing mark or an oncogene with an activation mark in a cancer condition.

An aspect of the invention provides a method of identifying a tumour suppressor gene comprising;
    contacting biological fluid sample obtained from an individual having a cancer condition with an antibody which binds specifically to a histone having a modification associated with silencing,
    isolating nucleosomes bound to said antibody, sequencing DNA associated with said bound nucleosomes; and,
    identifying said DNA as a tumor suppressor gene.

A method may comprise comparing said DNA with DNA associated with said bound nucleosomes in sample from a healthy individual (i.e. an individual not having a cancer condition). A DNA sequence which is associated with a silencing mark in the cancer sample but not the non-cancer sample is a candidate tumour suppressor.

In some embodiments, a modification associated with silencing may exclude Lys 9 methylation of histone H3.

A method may include concentrating the nucleosomes in the sample by a method other than collection on a poly K or streptavidin-coated support, prior to contacting with the antibody.

A method of identifying a tumour suppressor gene may include contacting the nucleosomes with a first antibody which binds specifically to a histone having a modification associated with silencing and a second antibody which binds to nucleosomes, for example in a sandwich assay format.

An aspect of the invention provides a method of identifying an oncogene comprising;
    contacting biological fluid sample obtained from an individual suffering from a cancer condition with an antibody which binds specifically to a histone having a modification associated with activation,
    isolating nucleosomes bound to said antibody,
    sequencing DNA associated with said bound nucleosomes, and;
    identifying said DNA as an oncogene.

Modifications associated with gene activation are described in more detail above. In some embodiments, a modification associated with activation may exclude H3 Lys 4 (Me), H3 Lys 9 (Ac) and/or H4 Lys 5(Ac).

A method may comprise comparing said DNA with DNA associated with said bound nucleosomes in sample from a healthy individual (i.e. an individual not having a cancer condition). A DNA sequence which is associated with an activation mark in the cancer sample but not the non-cancer sample is a candidate oncogene.

A method may include concentrating the nucleosomes in the sample by a method other than collection on a polyK or strepavidin-coated support, prior to contacting with the antibody.

A method of identifying an oncogene may include contacting the nucleosomes with a first antibody which binds specifically to a histone having a modification associated with silencing and a second antibody which binds to nucleosomes, for example in a sandwich assay format.

Methods described herein may be useful in detecting chromatin alterations which are associated with a disease condition. Cell-free nucleosomes may be isolated from samples from healthy individuals and from individuals having a disease condition, using a modified histone specific antibody and optionally a nucleosome specific antibody, to generate a first and second pool of nucleosomes, respectively. Preferably, methods of detecting chromatin alterations associated with disease comprise contacting the nucleosomes with a first antibody which binds specifically to a histone having a modification and a second antibody which specifically binds to nucleosomes, for example in a sandwich assay format.

After isolation, the nucleic acid associated with the isolated nucleosomes may be isolated and/or purified from the first and second pools of nucleosomes to generate a first and second pool of purified nucleic acid. The purified nucleic acid in each pool is then analyzed, using standard molecular techniques such as DNA sequencing, nucleic acid hybridization analysis (including Southern blot analysis), PCR amplification or differential screening, to identify differences between the two pools of nucleic acid sequences. Those nucleic acid sequences that are present in only one of the two pools represent nucleic acid sequences that are potentially related to the disease condition.

For example, the pools of nucleic acid sequences may be separately contacted with identical sets of DNA microarrays under conditions that allow for hybridization between complementary sequences. The microarrays may, for example, contain a subset of sequences that are associated with particular diseases (such as various known oncogene and tumor suppressor genes) or may contain the entire set of expressed sequences for one or more particular cell types and developmental stages. Hybridisation between a sequence in the pool of nucleosome associated nucleic acid and a nucleic acid sequence immobilised within the microarray produces a detectable signal, which allows the nucleosome associated nucleic acid to be identified. Suitable microarrays can be prepared using techniques known to those skilled in the art.

In some embodiments, the pools of nucleosome-associated nucleic acid may be amplified by PCR and/or labelled prior to contacting them with the microarray. Washing of the microarray removes non-bound and non-specifically bound material and allows detection of the labelled sequences that have specifically hybridised to sequences present on the microarray, thus identifying of the labelled sequences. Comparison of the hybridisation patterns obtained with the first and second pools of nucleosome-associated nucleic acid allows the identification of chromatin alterations that are potentially associated with a disease condition.

Pools of nucleosomes may be compared using a gene chip, DNA microarray, or a proteomics chip using standard techniques known to those skilled in the art (For example, WO 01/16860, WO 01/16860, WO 01/05935, WO 00/79326, WO 00/73504, WO 00/71746 and WO 00/53811).

Methods as described herein also allow the identification of genomic DNA which is associated with particular markers. DNA which is associated with a nucleosome having a particular histone modification may, for example, be immobilized on a solid surface or "chip". This DNA may, for example, represent all the nucleic acid sequences of a given cell that is competent for transcription or not competent for transcription, depending on the histone modification (for example, active: H3 lys 4 (Me), inactive: H3 lys 9 (Me).

Other aspects of the invention relate to the identification and monitoring of patients having disease conditions which are associated with the aberrant marking of histones.

A method of identifying a patient as a responsive to histone modification modulation therapy may comprise;
determining the level of histone modification in cell-free nucleosomes within a sample obtained from the patient, relative to a sample obtained from a healthy individual,
a change, for example an increase or decrease, in the level of modification being indicative that the patient is responsive to histone modification modulation therapy.

Methods of the invention may also be used to monitor the effect of histone modification modulation therapy. Histone modification modulation therapy may include, for example, inhibition of histone modifying or de-modifying enzymes, such as histone methyl transferases, acetylases and deacetylases.

A method of monitoring the effect of histone modification modulation therapy in a patient may comprise;
contacting samples obtained from the patient at first and second time points in said therapy with an antibody which specifically binds to a histone having a modification; and
determining binding of said antibody to said samples;
a change, for example an increase or decrease, in the binding of said antibody to the sample obtained at the second time point relative to the first being indicative of the effect of said therapy.

A patient may be suffering from a cancer or autoimmune condition, as described above.

For example, tumour cells may over-express enzymes that remove acetyl marks, leading to reduced expression of tumour suppressor genes (Johnstone R W (2002) Nature Reviews Drug Discovery, 1, 287). Patients identified using the present methods as having reduced histone acetylation may be treated with an agent which inhibits histone deacetylating enzymes. This increases histone acetylation, thereby increasing expression of tumor suppressor genes. The effect of therapy may be monitored by determining an increase in the level or amount of acetylation marks.

Aurora kinase B, which phosphorylates of H3 Ser 10, is over-expressed in many cancer conditions. Aurora kinase B inhibitors have been shown to have an anti-proliferative effect which is associated with inhibition of this histone marking step (Ditchfield C (2003) J. Cell Biol. 161, 267). Patients with increased phosphorylation at H3 Ser 10 may be identified using methods of the invention and the effects of treatment with an aurora kinase inhibitor monitored.

Other aspects of the invention relate to the analysis of the DNA associated with specifically marked nucleosomes in order to identify the appropriate treatment regimes.

For example, such analysis may indicate the propensity of a tumour to metastasise, the hormone dependence of a tumour, or the activation in a tumour of certain resistance genes and pathways, for example, glutathione S-transferase-pi(Townsend D and Tew K (2003) Am J Pharmacogenomics 3, 157-172), multidrug resistance associated protein, p-glycoprotein (Mattern J (2003) Anticancer Res 23, 1769-1772) and glyoxalase-I(Tsuruo T (2003) Cancer Sci 94, 15-21). The effect of treatment regimes could be monitored, for example, by observing changes in gene silencing/activation marks associated with these genes.

A method of assessing a patient for a therapeutic treatment may comprise;
determining the presence of one or more genes which confer resistance to said treatment in a cell-free nucleosome in a sample obtained from the patient, as described above,
wherein said nucleosome comprises or contains a histone modification associated with activation or silencing.

Histone modifications associated with activation or silencing are described in more detail above.

Various further aspects and embodiments of the present invention will be apparent to those skilled in the art in view of the present disclosure. All documents referenced in this specification are incorporated herein by reference.

All combinations and sub-combinations of the features described above, whether or not specifically described or exemplified, are encompassed by the invention.

Certain aspects and embodiments of the invention will now be illustrated by way of example and with reference to the figures and table described below.

Figure 1:
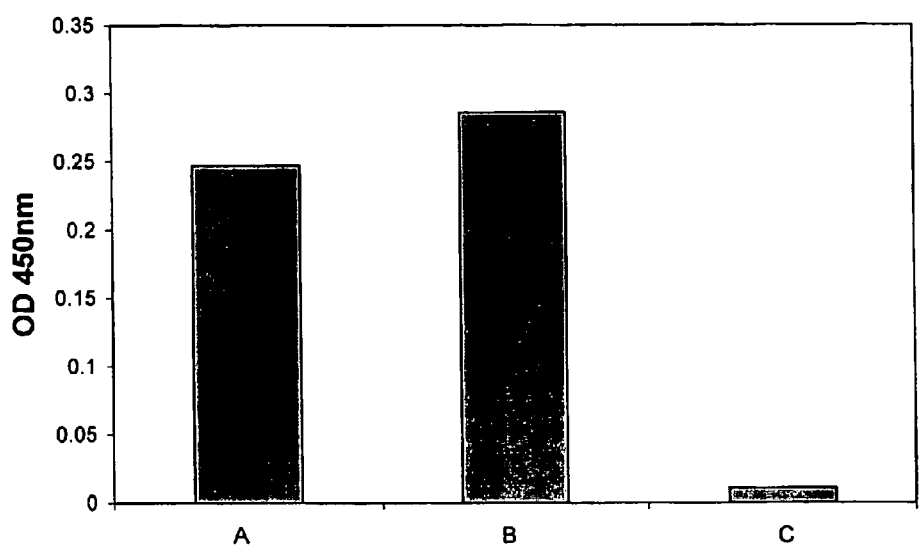
FIG. 1 shows the efficient recovery and detection of marked (dimethylated Lys 4 of histone H3) chicken nucleosomes spiked into human blood. Column A shows platelet poor plasma (PPP) derived from normal blood spiked with chicken nucleosomes, column B shows buffer spiked with chicken nucleosomes and column C shows PPP derived from normal blood.

Table 1 shows a list of known histone marks. In the table, Me=mono, di or trimethyl, Ac=Acetyl, Phos=Phosphorylation, Ubiq=Ubiquitinated (For Arg, Me can mean mono or dimethylated, where dimethylation can be symmetrical or asymmetrical).

Table 2 shows examples of preferred marks according to the invention. As for table 1, Me=mono, di or trimethyl, Ac=Acetyl, Phos=Phosphorylation, Ubiq=Ubiquitinated (For Arg, Me can mean mono or dimethylated, where dimethylation can be symmetrical or asymmetrical).

Table 3 shows examples of peptides which may be used to generate modified histone specific antibodies.

EXAMPLES

Materials and Methods
Collection and Preparation of Blood Samples 20 ml of blood were withdrawn by venepuncture into vacutainer tubes containing sodium citrate, which were then kept on ice. Platelet rich plasma (PRP) was prepared within 4 hours of blood collection by centrifugation at 4° C. at 300 g for 20 minutes. An appropriate volume of 20× inhibitor cocktail was added directly to the resultant PRP (resulting in supramaximal concentrations of okadaic acid, cypermethrin, staurosporine, trichostatin A, AEBSF, aprotinin, E-64, EDTA and leupeptin). Platelet poor plasma (PPP) was generated by centrifugation of the PRP on a Percoll underlay at 1500 g for a further 20 minutes.

Concentration of Plasma Samples

In some experiments, the nucleosomes in patient and normal plasma samples were concentrated prior to analysis as follows:—

Plasma samples (1.1 ml), collected and prepared as described above, were diluted with 2.4 ml of Dulbeccos PBS (not containing $Ca^{2+}$ or $Mg^{2+}$). The samples were centrifuged at ca. 328,000 g at 4° C. for 1.5 hours. The supernatants were removed and the pellets resuspended in 100 μl of 10 mM EDTA, vortexed and left at room temperature for 20 minutes. Cell lysis buffer (190 μl), supplemented with the same inhibitor cocktail and 334 μg/ml HBR-1 (heterophilic blocking reagent, Scantibodies Laboratories Inc., San Diego), was added and incubated at room temperature for 1 hour prior to analysis by ELISA.

Note: the same ratio of EDTA:lysis buffer, containing the same concentrations of inhibitors and HBR-1, is used as the ELISA diluent for both the patient samples and standard curve samples.

In some experiments, the standard curve was prepared in the presence of a preparation of concentrated, pooled normal plasma.

ELISA on Nucleosomes from Human Blood Samples

Method 1

A Nunc Maxisorp 96-well ELISA plate was coated overnight at 4° C. with a purified mouse anti-nucleosome monoclonal antibody at a concentration of 2.5 μg/ml in a carbonate/bicarbonate buffer pH 9.5, 50 μl/well added (125 ng/well). The contents of the plate were flicked out and washed three times with PBS (Dulbecco A). Blocking buffer (1% BSA in PBS+0.05% Tween 20) was then added.

PPP derived from normal blood which had been spiked with chicken nucleosomes or buffer spiked with chicken nucleosomes, were diluted appropriately with blocking buffer.

The block buffer was removed from the ELISA plate and diluted samples (for example 50 μl) were transferred to the plate. Appropriate control wells were prepared.

The plate was sealed transferred to a shaking incubator (30° C.) for a period of 2 hours. The plate was flicked out and washed 4 times with PBS.

Anti-mark detection antibodies were appropriately diluted in block buffer and added to designated wells of the plate (typically 50 μl/well). The plates were sealed and returned to the shaking incubator for a further 1.5 hours. The plates were washed as for the previous step, followed by the addition of, for example, 50 μl of the anti-rabbit HRP conjugate to all wells, then returned to the incubator for 1 hour.

The wash step was repeated on the plates and 100 μl/well of SureBlue TMB Microwell peroxidase substrate was added to all wells. The plates were returned to the shaker/incubator to allow development of the blue colour, typically for 40 minutes. Finally, the reaction was stopped by the addition of TMB Stop Solution. The plates were read at a wavelength of 450 nM.

Method 2

A modified indirect sandwich ELISA was used to detect covalent modifications of histones of nucleosomes from human blood samples, concentrated as above.

A Nunc Maxisorp 96-well ELISA plate was coated overnight at 4° C. with a purified mouse anti-nucleosome monoclonal antibody at a concentration of 3.0 μg/ml in a carbonate/bicarbonate buffer pH 9.5, 50 μl/well added (125 ng/well). The contents of the plate were flicked out and washed three times with PBS (Dulbecco A). Blocking buffer (1% BSA in Ultrablock+0.05% Tween 20) was then added for 1 hour.

Concentrated PPP samples were serially diluted with ELISA diluent.

The block buffer was removed from the ELISA plate and diluted samples (for example 50 μl) were transferred to the plate. Appropriate control wells were prepared.

The plate was sealed transferred to a shaking incubator (30° C.) for a period of 2 hours. The plate was flicked out and washed 4 times with PBS.

Detection antibodies were appropriately diluted and added to designated wells of the plate (typically 50 μl/well). The plates were sealed and returned to the shaking incubator for a further 1.5 hours. The plates were washed as for the previous step, followed by the addition of, for example, 50 μl of biotinylated anti-rabbit conjugate to all wells, then returned to the incubator for 1 hour. The wash step was repeated and streptavidin-HRP conjugate was added to all wells and the incubation continued for 0.5 hours.

The wash step was repeated on the plates and 100 μl/well of SureBlue TMB Microwell peroxidase substrate was added to all wells. The plates were returned to the shaker/incubator to allow development of the blue colour, typically for 20 minutes. Finally, the reaction was stopped by the addition of TMB Stop Solution. The plates were read at a wavelength of 450 nM.

Results

Spiking of Normal Blood with Nucleosomes

Using the sandwich ELISA described in Method 1 and an antibody to dimethylated lysine 4 of histone H3 as the second antibody, samples of buffer spiked with chicken nucleosomes and PPP derived from normal blood which had been spiked with chicken nucleosomes generated equivalent signals (FIG. 1). No significant signal was obtained from PPP derived from normal blood that had not been spiked with chicken nucleosomes over the dilution range used in the assay (FIG. 1).

Spiking of Buffer with Nucleosomes

Figure 2:
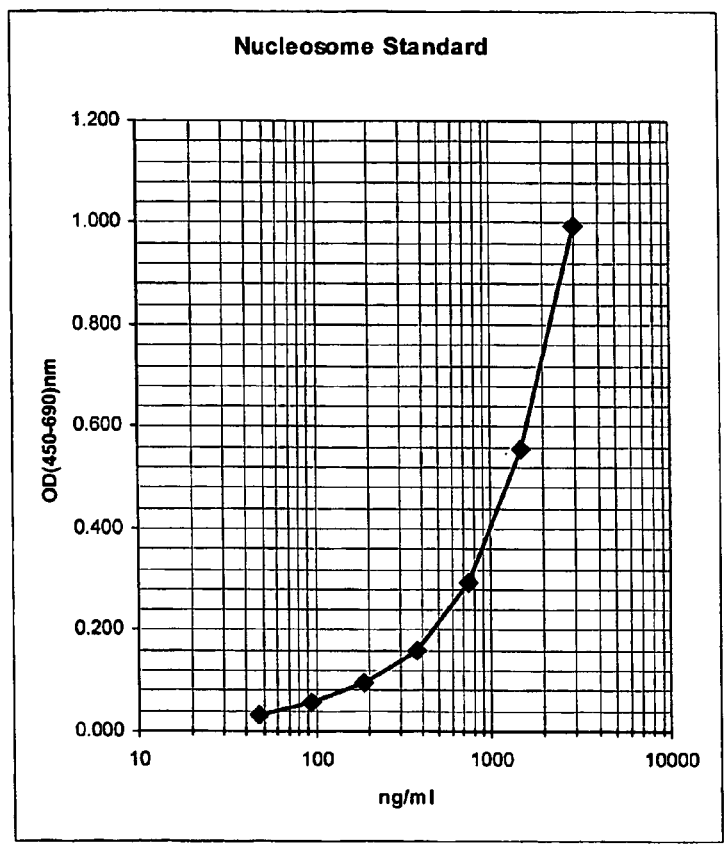
FIG. 2 shows an ELISA standard curve for chicken nucleosomes spiked into buffer, detected using an antibody to dimethylated Lys 4 of histone H3.

Using the sandwich ELISA described in Method 2 and an antibody to dimethylated lysine 4 of histone H3 as the second antibody, samples of buffer spiked with chicken nucleosomes were shown to generate a standard curve (FIG. 2).

Analysis of Patient Samples

Figure 3:
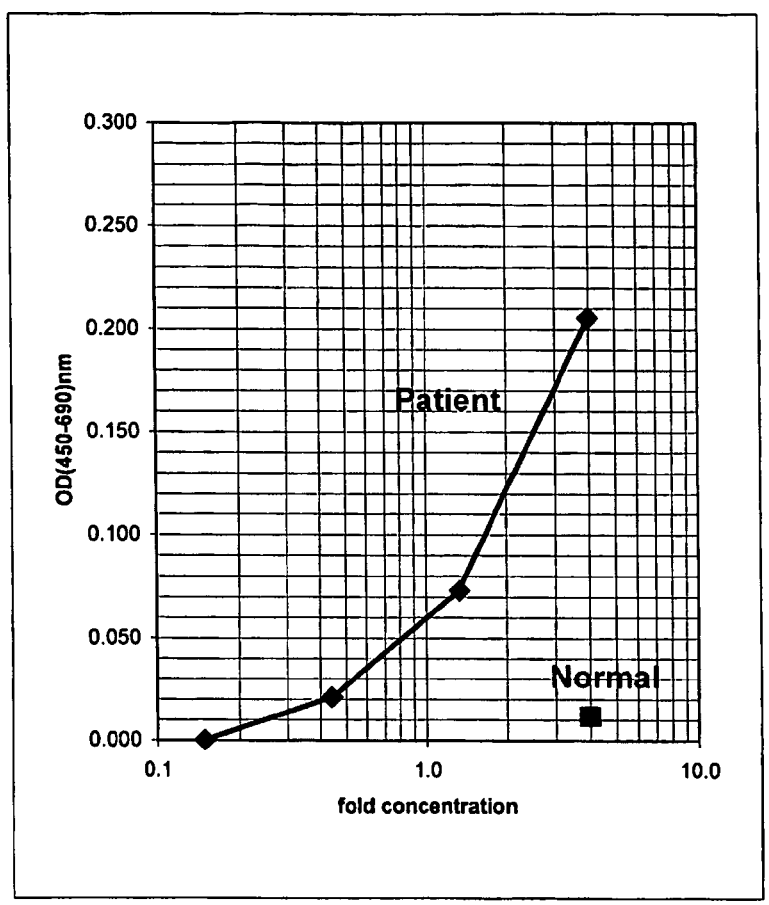
FIG. 3 shows the analysis of a concentrated plasma sample from a patient with cancer and of a concentrated normal plasma sample using an antibody to dimethylated Lys 4 of histone H3.

Using the concentration method described above, the sandwich ELISA described in Method 2 and an antibody to histone H3 dimethyl lysine 4 as the second antibody in the ELISA, an increasing signal is measured as the concentration of the sample derived from a patient increases (FIG. 3). In contrast, a concentrated plasma sample from pooled normal individuals, failed to generate a signal at the highest concentration (FIG. 3).

TABLE 1

| Histone | Residue | Modification |
|---------|---------|--------------|
| H3 | Arg 2 | Me |
| H3 | Arg 17 | Me |
| H3 | Arg 26 | Me |
| H3 | Lys 4 | Me |
| H3 | Lys 9 | Me |
| H3 | Lys 14 | Me |
| H3 | Lys 23 | Me |
| H3 | Lys 27 | Me |
| H3 | Lys 36 | Me |
| H3 | Lys 79 | Me |
| H3 | Lys 9 | Ac |
| H3 | Lys 14 | Ac |
| H3 | Lys 18 | Ac |

TABLE 1-continued

| Histone | Residue | Modification |
|---|---|---|
| H3 | Lys 23 | Ac |
| H3 | Lys 27 | Ac |
| H3 | Lys 115 | Ac |
| H3 | Lys 122 | Ac |
| H3 | Ser 10 | Phos |
| H3 | Ser 28 | Phos |
| H3 | Thr 3 | Phos |
| H3 | Thr 11 | Phos |
| H3 | Thr 118 | Phos |
| H4 | Arg 3 | Me |
| H4 | Arg 92 | Me |
| H4 | Lys 12 | Me |
| H4 | Lys 20 | Me |
| H4 | Lys 59 | Me |
| H4 | Lys 79 | Me |
| H4 | Lys 5 | Ac |
| H4 | Lys 8 | Ac |
| H4 | Lys 12 | Ac |
| H4 | Lys 16 | Ac |
| H4 | Lys 20 | Ac |
| H4 | Lys 77 | Ac |
| H4 | Lys 79 | Ac |
| H4 | Ser 1 | Phos |
| H4 | Ser 47 | Phos |
| H2A | Lys 99 | Me |
| H2A | Lys 5 | Ac |
| H2A | Lys 9 | Ac |
| H2A | Lys 13 | Ac |
| H2A | Lys 15 | Ac |
| H2A | Lys 36 | Ac |
| H2A | Lys 119 | Ac |
| H2A | Ser 1 | Phos |
| H2A | Lys 119 | Ubiq |
| H2B | Arg 99 | Me |
| H2B | Lys 5 | Me |
| H2B | Lys 23 | Me |
| H2B | Lys 43 | Me |
| H2B | Lys 5 | Ac |
| H2B | Lys 12 | Ac |
| H2B | Lys 15 | Ac |
| H2B | Lys 20 | Ac |
| H2B | Lys 24 | Ac |
| H2B | Lys 85 | Ac |
| H2B | Lys 108 | Ac |
| H2B | Lys 116 | Ac |
| H2B | Lys 120 | Ac |
| H2B | Ser 14 | Phos |
| H2B | Ser 32 | Phos |
| H2B | Ser 36 | Phos |
| H2B | Lys 120 | Ubiq |
| H2A.X | Ser 1 | Phos |
| H2A.X | Ser 139 | Phos |
| H2A.X | Thr 136 | Phos |
| H2A.X | Lys 119 | Ubiq |
| H2A.X | Lys 5 | Ac |
| H2A.X | Lys 9 | Ac |
| H3.3 | Arg 2 | Me |
| H3.3 | Arg 17 | Me |
| H3.3 | Arg 26 | Me |
| H3.3 | Lys 4 | Me |
| H3.3 | Lys 9 | Me |
| H3.3 | Lys 14 | Me |
| H3.3 | Lys 18 | Me |
| H3.3 | Lys 27 | Me |
| H3.3 | Lys 36 | Me |
| H3.3 | Lys 37 | Me |
| H3.3 | Lys 79 | Me |
| H3.3 | Lys 9 | Ac |
| H3.3 | Lys 14 | Ac |
| H3.3 | Lys 18 | Ac |
| H3.3 | Lys 23 | Ac |
| H3.3 | Lys 27 | Ac |
| H3.3 | Ser 10 | Phos |
| H3.3 | Ser 28 | Phos |
| H3.3 | Thr 11 | Phos |

TABLE 2

| Histone | Residue | Modification |
|---|---|---|
| H3 | Arg 2 | Me |
| H3 | Arg 17 | Me |
| H3 | Arg 26 | Me |
| H3 | Lys 14 | Me |
| H3 | Lys 23 | Me |
| H3 | Lys 79 | Me |
| H3 | Lys 9 | Ac |
| H3 | Lys 14 | Ac |
| H3 | Lys 18 | Ac |
| H3 | Lys 23 | Ac |
| H3 | Lys 27 | Ac |
| H3 | Lys 115 | Ac |
| H3 | Lys 122 | Ac |
| H3 | Ser 10 | Phos |
| H3 | Ser 28 | Phos |
| H3 | Thr 3 | Phos |
| H3 | Thr 11 | Phos |
| H3 | Thr 118 | Phos |
| H4 | Arg 92 | Me |
| H4 | Lys 12 | Me |
| H4 | Lys 59 | Me |
| H4 | Lys 79 | Me |
| H4 | Lys 8 | Ac |
| H4 | Lys 12 | Ac |
| H4 | Lys 16 | Ac |
| H4 | Lys 20 | Ac |
| H4 | Lys 77 | Ac |
| H4 | Lys 79 | Ac |
| H4 | Ser 1 | Phos |
| H4 | Ser 47 | Phos |
| H2A | Lys 99 | Me |
| H2A | Lys 5 | Ac |
| H2A | Lys 9 | Ac |
| H2A | Lys 13 | Ac |
| H2A | Lys 15 | Ac |
| H2A | Lys 36 | Ac |
| H2A | Lys 119 | Ac |
| H2A | Ser 1 | Phos |
| H2A | Lys 119 | Ubiq |
| H2B | Arg 99 | Me |
| H2B | Lys 5 | Me |
| H2B | Lys 23 | Me |
| H2B | Lys 43 | Me |
| H2B | Lys 5 | Ac |
| H2B | Lys 12 | Ac |
| H2B | Lys 15 | Ac |
| H2B | Lys 20 | Ac |
| H2B | Lys 24 | Ac |
| H2B | Lys 85 | Ac |
| H2B | Lys 108 | Ac |
| H2B | Lys 116 | Ac |
| H2B | Lys 120 | Ac |
| H2B | Ser 32 | Phos |
| H2B | Ser 36 | Phos |
| H2B | Lys 120 | Ubiq |
| H2A.X | Ser 1 | Phos |
| H2A.X | Ser 139 | Phos |
| H2A.X | Thr 136 | Phos |
| H2A.X | Lys 119 | Ubiq |
| H2A.X | Lys 5 | Ac |
| H2A.X | Lys 9 | Ac |
| H3.3 | Arg 2 | Me |
| H3.3 | Arg 17 | Me |
| H3.3 | Arg 26 | Me |
| H3.3 | Lys 4 | Me |
| H3.3 | Lys 9 | Me |
| H3.3 | Lys 14 | Me |
| H3.3 | Lys 18 | Me |
| H3.3 | Lys 27 | Me |
| H3.3 | Lys 36 | Me |
| H3.3 | Lys 37 | Me |
| H3.3 | Lys 79 | Me |
| H3.3 | Lys 9 | Ac |
| H3.3 | Lys 14 | Ac |
| H3.3 | Lys 18 | Ac |
| H3.3 | Lys 23 | Ac |
| H3.3 | Lys 27 | Ac |
| H3.3 | Ser 10 | Phos |

TABLE 2-continued

| Histone | Residue | Modification |
|---------|---------|--------------|
| H3.3 | Ser 28 | Phos |
| H3.3 | Thr 11 | Phos |

TABLE 3

| | | |
|---|---|---|
| H3 lys 4 (Me): | ARTK(M)QTAR | (SEQ ID NO: 1) |
| H4 arg 3 (Me): | SGR(M)GK | (SEQ ID NO: 2) |
| H4 lys 5 (Ac): | SGRGK(A) | (SEQ ID NO: 3) |
| H3 lys 9 (Me): | QTARK(M)STGV | (SEQ ID NO: 6) |
| H2B ser 14 (Phos): | SAPAPKKGS(P)KK | (SEQ ID NO: 7) |
| H3 lys 27 (Me): | AARK(M)SAPVCG | (SEQ ID NO: 8) |
| H3 lys 36 (Me): | SGGVK(M)KPHKCG | (SEQ ID NO: 9) |
| H4 lys 20 (Me): | RHRK(M)ILRDCG | (SEQ ID NO: 10) |
| H4 arg 3 (Me)/lys 5 (Ac): | SGR(M)GK(A) | (SEQ ID NO: 4) |
| H4 Ser 2 (phos)/Arg 3 (me)/Lys 5 (Ac): | S(P)GR(M)GK(A) | (SEQ ID NO: 5) |

REPRESENTATIVE HISTONE SEQUENCES

Human H3 histone (SEQ ID NO:11)
ARTKQTARKSTGGKAPRKQLATKAARK-SAPATGGVKKPHRYRPGTVALREIRRYQKST ELLIRKLPFQRLVREIAQDFKTDLRFQS-SAVMALQEASEAYLVGLFEDTNLCAIHAKRVT IMPKDIQLARRIRGERA Human H4 histone (SEQ ID NO:12)
SGRGKGGKGLGKGGAKRHRKVLRD-DIQGITKPAIRRLARRGGVKRISGLIYEETRGVLK V FLENVIRDAVTYTEHAKRKTVTAMDVVY-ALKRQGRTLYGFGG Human H2A histone (SEQ ID NO:13)
SGRGKQGGKARAKAKTRSSRAGLQF-PVGRVHRLLRKGNYAERVGAGAPVYLAAVLEYLTA EILELAGNAARDNKKTRI-IPRHLQLAIRNDEELNKLLGKVTIAQG-GVLPNIQAVLLPKKTESHHKA KGK Human H2B histone (SEQ ID NO:14)
PEPSKSAPAPKKGSKKAIT-KAQKKDGKKRKRSRKESYSIYVYKV-LKQVHPDTGISSKAM GIMNSFVNDIFERIAGEASR-LAHYNKRSTITSREIQTAVRLLLPGELAKHAVSEGTK-AVTK YTSSK Human H2A.X histone (SEQ ID NO:15)
SGRGKTGGKARAKAKSRSSRAGLQF-PVGRVHRLLRKGHYAERVGAGAPVYLAAVLEY LTA EILELAGNAARDNKKTRI-IPRHLQLAIRNDEELNKLLGGVTIAQG-GVLPNIQAVLLPKKTS ATVGPKAPSG-GKKATQASQEY Human H3.3 histone (SEQ ID NO:16)
ARTKQTARKSTGGKAPRKQLATKAARK-SAPSTGGVKKPHRYRPGTVALREIRRYQKST ELLIRKLPFQRLVREIAQDFKTDLR-FQSAAIGALQEASEAYLVGLFEDTNLCAIHAKRVTI MPKDIQLARRIRGERA

The invention claimed is:

1. A method of assessing histone modification in a sample, the method comprising:
   contacting a biological fluid sample with a first antibody that binds to nucleosomes, wherein the first antibody binds specifically to one or more unmodified nucleosome components, and;
   determining binding of said first antibody to a nucleosome using a second antibody which binds to a histone modification.

2. A method of assessing histone modification in a sample, the method comprising:
   contacting a biological fluid sample with a first antibody that specifically binds to a histone modificaiton, and;
   determining binding of said first antibody to a nucleosome containing a histone modification using a second antibody that binds to nucleosomes,
   wherein the second antibody binds specifically to one or more unmodified nucleosome components.

3. A method of detecting the presence of a nucleosome containing a modified histone in a biological fluid sample the method comprising:
   contacting a biological fluid sample with a first antibody that specifically binds to an unmodified histone or DNA in a cell free nucleosomes present in said sample under conditions that will form a first complex of first antibody bound to said nucleosomes,
   contacting histones of the nucleosome of the first complex with a second antibody which specifically binds to a histone modification in the cell free nucleosome, said first antibody and said second antibody being different, and
   determining the presence in said sample of nucleosomes containing a histone modification from the binding of said second antibody to said first complex.

4. A method of detecting the presence of a nucleosome containing a histone modification in a biological fluid sample, the method comprising:
   contacting a biological fluid sample with a first antibody which specifically binds to a histone modification in a cell free nucleosome under conditions that will form a first complex of first antibody bound to said cell free nucleosome,
   contacting the nucleosome of the first complex with a second antibody that specifically binds to an unmodified histone or DNA in the cell free nucleosome, said first antibody and said second antibody being different, and
   determining the presence of nucleosomes containing a histone modification in said sample from the binding of said second antibody to said first complex.

5. The method according to claim 1 wherein the histone modification is selected from the group consisting of:
   (a) methylation of H3 at an arginine residue corresponding to the arginine residue at position 2, 17 or 26 of SEQ ID NO:11;
   (b) methylation of H3 at a lysine residue corresponding to the lysine residue at position 4, 9, 14, 23, 27, 36, or 79 of SEQ ID NO:11;
   (c) acetylation of H3 at a lysine residue corresponding to the lysine residue at position 9, 14, 18, 23, 27, 115 or 122 of SEQ ID NO:11;
   (d) phosphorylation of H3 at a serine residue corresponding to the serine residue at position 10 or 28 of SEQ ID NO:11;

(e) phosphorylation of H3 at a threonine residue corresponding to the threonine residue at position 3, 11 or 118 of SEQ ID NO:11;
(f) methylation of H4 at an arginine residue corresponding to the arginine residue at position 3 or 92 of SEQ ID NO:12;
(g) methylation of H4 at a lysine residue corresponding to the lysine residue at position 12, 20, 59 or 79 of SEQ ID NO:12;
(h) acetylation of H4 at a lysine residue corresponding to the lysine residue at position 5, 8, 12, 16, 20, 77 or 79 of SEQ ID NO:12;
(i) phosphorylation of H4 at a serine residue corresponding to the serine residue at position 1 or 47 of SEQ ID NO:12;
(j) methylation of H2A at a lysine residue corresponding to the lysine residue at position 99 of SEQ ID NO:13;
(k) acetylation of H2A at a lysine residue corresponding to the lysine residue at position 5, 9, 13, 15, 36 or 119 of SEQ ID NO:13;
(l) phosphorylation of H2A at a serine residue corresponding to the serine residue at position 1 of SEQ ID NO:13;
(m) ubiquitination of H2A at a lysine residue corresponding to the lysine residue at position 119 of SEQ ID NO:14;
(n) methylation of H2B at an arginine residue corresponding to the arginine residue at position 99 of SEQ ID NO:14;
(o) methylation of H2B at a lysine residue corresponding to the lysine residue at position 5, 23 or 43 of SEQ ID NO:14;
(p) acetylation of H2B at a lysine residue corresponding to the lysine residue at position 5, 12, 15, 20, 24, 85, 108, 116 or 120 of SEQ ID NO:14;
(q) phosphorylation of H2B at a serine residue corresponding to the serine residue at position 14, 32 or 36 of SEQ ID NO:14;
(r) ubiquitination of H2B at a lysine residue corresponding to the lysine residue at position 120 of SEQ ID NO:14;
(s) phosphorylation of H2A.X at a serine residue corresponding to the serine residue at position 1 or 139 of SEQ ID NO:15;
(t) phosphorylation of H2A.X at a threonine residue corresponding to the threonine residue at position 136 of SEQ ID NO:15;
(u) ubiquitination of H2A.X at a lysine residue corresponding to the lysine residue at position 119 of SEQ ID NO:15;
(v) acetylation of H2A.X at a lysine residue corresponding to the lysine residue at position 5 or 9 of SEQ ID NO:15;
(w) methylation of H3.3 at an arginine residue corresponding to the arginine residue at position 2, 17 or 26 of SEQ ID NO: 16;
(x) methylation of H3.3 at a lysine residue corresponding to the lysine residue at position 4, 9, 14, 18, 27, 36, 37 or 79 of SEQ ID NO: 16;
(y) acetylation of H3.3 at a lysine residue corresponding to the lysine residue at position 9, 14, 18, 23 or 27 of SEQ ID NO:16;
(z) phosphorylation of H3.3 at a serine residue corresponding to the serine residue at position 10 or 28 of SEQ ID NO:16; and
(aa) phosphorylation of H3.3 at a threonine residue corresponding to the threonine residue at position 11 of SEQ ID NO:16.

6. The method according to claim 1 wherein the biological fluid sample is a blood, plasma, serum, lymph, urine, synovial fluid, spinal fluid, saliva, or mucoussample.
7. The method according to claim 1 wherein said first antibody or said second antibody is immobilised.
8. The method according to claim 7 wherein the non-immobilised antibody of said first antibody and second antibody comprises a detectable label.
9. The method according to claim 2 wherein the histone modification is selected from the group consisting of:
(a) methylation of H3 at an arginine residue corresponding to the arginine residue at position 2, 17 or 26 of SEQ ID NO:11;
(b) methylation of H3 at a lysine residue corresponding to the lysine residue at position 4, 9, 14, 23, 27, 36, or 79 of SEQ ID NO:11;
(c) acetylation of H3 at a lysine residue corresponding to the lysine residue at position 9, 14, 18, 23, 27, 115 or 122 of SEQ ID NO:11;
(d) phosphorylation of H3 at a serine residue corresponding to the serine residue at position 10 or 28 of SEQ ID NO:11;
(e) phosphorylation of H3 at a threonine residue corresponding to the threonine residue at position 3, 11 or 118 of SEQ ID NO:11;
(f) methylation of H4 at an arginine residue corresponding to the arginine residue at position 3 or 92 of SEQ ID NO:12;
(g) methylation of H4 at a lysine residue corresponding to the lysine residue at position 12, 20, 59 or 79 of SEQ ID NO:12;
(h) acetylation of H4 at a lysine residue corresponding to the lysine residue at position 5, 8, 12, 16, 20, 77 or 79 of SEQ ID NO:12;
(i) phosphorylation of H4 at a serine residue corresponding to the serine residue at position 1 or 47 of SEQ ID NO:12;
(j) methylation of H2A at a lysine residue corresponding to the lysine residue at position 99 of SEQ ID NO:13;
(k) acetylation of H2A at a lysine residue corresponding to the lysine residue at position 5, 9, 13, 15, 36 or 119 of SEQ ID NO:13;
(l) phosphorylation of H2A at a serine residue corresponding to the serine residue at position 1 of SEQ ID NO:13;
(m) ubiquitination of H2A at a lysine residue corresponding to the lysine residue at position 119 of SEQ ID NO:14;
(n) methylation of H2B at an arginine residue corresponding to the arginine residue at position 99 of SEQ ID NO:14;
(o) methylation of H2B at a lysine residue corresponding to the lysine residue at position 5, 23 or 43 of SEQ ID NO:14;
(p) acetylation of H2B at a lysine residue corresponding to the lysine residue at position 5, 12, 15, 20, 24, 85, 108, 116 or 120 of SEQ ID NO:14;
(q) phosphorylation of H2B at a serine residue corresponding to the serine residue at position 14, 32 or 36 of SEQ ID NO:14;
(r) ubiquitination of H2B at a lysine residue corresponding to the lysine residue at position 120 of SEQ ID NO:14;
(s) phosphorylation of H2A.X at a serine residue corresponding to the serine residue at position 1 or 139 of SEQ ID NO:15;
(t) phosphorylation of H2A.X at a threonine residue corresponding to the threonine residue at position 136 of SEQ ID NO:15;

(u) ubiquitination of H2A.X at a lysine residue corresponding to the lysine residue at position 119 of SEQ ID NO:15;
(v) acetylation of H2A.X at a lysine residue corresponding to the lysine residue at position 5 or 9 of SEQ ID NO:15;
(w) methylation of H3.3 at an arginine residue corresponding to the arginine residue at position 2, 17 or 26 of SEQ ID NO: 16;
(x) methylation of H3.3 at a lysine residue corresponding to the lysine residue at position 4, 9, 14, 18, 27, 36, 37 or 79 of SEQ ID NO: 16;
(y) acetylation of H3.3 at a lysine residue corresponding to the lysine residue at position 9, 14, 18, 23 or 27 of SEQ ID NO:16;
(z) phosphorylation of H3.3 at a serine residue corresponding to the serine residue at position 10 or 28 of SEQ ID NO:16; and
(aa) phosphorylation of H3.3 at a threonine residue corresponding to the threonine residue at position 11 of SEQ ID NO:16.

10. The method according to claim 2 wherein the biological fluid sample is a blood, plasma, serum, lymph, urine, synovial fluid, spinal fluid, saliva, or mucous sample.

11. The method according to claim 2 wherein said first antibody or said second antibody is immobilised.

12. The method according to claim 11 wherein the non-immobilised antibody of said first antibody and second antibody comprises a detectable label.

13. The method according to claim 3 wherein the histone modification is selected from the group consisting of:
(a) methylation of H3 at an arginine residue corresponding to the arginine residue at position 2, 17 or 26 of SEQ ID NO:11;
(b) methylation of H3 at a lysine residue corresponding to the lysine residue at position 4, 9, 14, 23, 27, 36, or 79 of SEQ ID NO:11;
(c) acetylation of H3 at a lysine residue corresponding to the lysine residue at position 9, 14, 18, 23, 27, 115 or 122 of SEQ ID NO:11;
(d) phosphorylation of H3 at a serine residue corresponding to the serine residue at position 10 or 28 of SEQ ID NO:11;
(e) phosphorylation of H3 at a threonine residue corresponding to the threonine residue at position 3, 11 or 118 of SEQ ID NO:11;
(f) methylation of H4 at an arginine residue corresponding to the arginine residue at position 3 or 92 of SEQ ID NO:12;
(g) methylation of H4 at a lysine residue corresponding to the lysine residue at position 12, 20, 59 or 79 of SEQ ID NO:12;
(h) acetylation of H4 at a lysine residue corresponding to the lysine residue at position 5, 8, 12, 16, 20, 77 or 79 of SEQ ID NO:12;
(i) phosphorylation of H4 at a serine residue corresponding to the serine residue at position 1 or 47 of SEQ ID NO:12;
(j) methylation of H2A at a lysine residue corresponding to the lysine residue at position 99 of SEQ ID NO:13;
(k) acetylation of H2A at a lysine residue corresponding to the lysine residue at position 5, 9, 13, 15, 36 or 119 of SEQ ID NO:13;
(l) phosphorylation of H2A at a serine residue corresponding to the serine residue at position 1 of SEQ ID NO:13;
(m) ubiquitination of H2A at a lysine residue corresponding to the lysine residue at position 119 of SEQ ID NO:14;
(n) methylation of H2B at an arginine residue corresponding to the arginine residue at position 99 of SEQ ID NO:14;
(o) methylation of H2B at a lysine residue corresponding to the lysine residue at position 5, 23 or 43 of SEQ ID NO:14;
(p) acetylation of H2B at a lysine residue corresponding to the lysine residue at position 5, 12, 15, 20, 24, 85, 108, 116 or 120 of SEQ ID NO:14;
(q) phosphorylation of H2B at a serine residue corresponding to the serine residue at position 14, 32 or 36 of SEQ ID NO:14;
(r) ubiquitination of H2B at a lysine residue corresponding to the lysine residue at position 120 of SEQ ID NO:14;
(s) phosphorylation of H2A.X at a serine residue corresponding to the serine residue at position 1 or 139 of SEQ ID NO:15;
(t) phosphorylation of H2A.X at a threonine residue corresponding to the threonine residue at position 136 of SEQ ID NO:15;
(u) ubiquitination of H2A.X at a lysine residue corresponding to the lysine residue at position 119 of SEQ ID NO:15;
(v) acetylation of H2A.X at a lysine residue corresponding to the lysine residue at position 5 or 9 of SEQ ID NO:15;
(w) methylation of H3.3 at an arginine residue corresponding to the arginine residue at position 2, 17 or 26 of SEQ ID NO: 16;
(x) methylation of H3.3 at a lysine residue corresponding to the lysine residue at position 4, 9, 14, 18, 27, 36, 37 or 79 of SEQ ID NO: 16;
(y) acetylation of H3.3 at a lysine residue corresponding to the lysine residue at position 9, 14, 18, 23 or 27 of SEQ ID NO:16;
(z) phosphorylation of H3.3 at a serine residue corresponding to the serine residue at position 10 or 28 of SEQ ID NO:16; and
(aa) phosphorylation of H3.3 at a threonine residue corresponding to the threonine residue at position 11 of SEQ ID NO:16.

14. The method according to claim 3 wherein the biological fluid sample is a blood, plasma, serum, lymph, urine, synovial fluid, spinal fluid, saliva, or mucous sample.

15. The method according to claim 3 wherein said first antibody or said second antibody is immobilised.

16. The method according to claim 15 wherein the non-immobilised antibody of said first antibody and second antibody comprises a detectable label.

17. The method according to claim 4 wherein the histone modification is selected from the group consisting of:
(a) methylation of H3 at an arginine residue corresponding to the arginine residue at position 2, 17 or 26 of SEQ ID NO:11;
(b) methylation of H3 at a lysine residue corresponding to the lysine residue at position 4, 9, 14, 23, 27, 36, or 79 of SEQ ID NO:11;
(c) acetylation of H3 at a lysine residue corresponding to the lysine residue at position 9, 14, 18, 23, 27, 115 or 122 of SEQ ID NO:11;
(d) phosphorylation of H3 at a serine residue corresponding to the serine residue at position 10 or 28 of SEQ ID NO:11;
(e) phosphorylation of H3 at a threonine residue corresponding to the threonine residue at position 3, 11 or 118 of SEQ ID NO:11;

(f) methylation of H4 at an arginine residue corresponding to the arginine residue at position 3 or 92 of SEQ ID NO:12;
(g) methylation of H4 at a lysine residue corresponding to the lysine residue at position 12, 20, 59 or 79 of SEQ ID NO:12;
(h) acetylation of H4 at a lysine residue corresponding to the lysine residue at position 5, 8, 12, 16, 20, 77 or 79 of SEQ ID NO:12;
(i) phosphorylation of H4 at a serine residue corresponding to the serine residue at position 1 or 47 of SEQ ID NO:12;
(j) methylation of H2A at a lysine residue corresponding to the lysine residue at position 99 of SEQ ID NO:13;
(k) acetylation of H2A at a lysine residue corresponding to the lysine residue at position 5, 9, 13, 15, 36 or 119 of SEQ ID NO:13;
(l) phosphorylation of H2A at a serine residue corresponding to the serine residue at position 1 of SEQ ID NO:13;
(m) ubiquitination of H2A at a lysine residue corresponding to the lysine residue at position 119 of SEQ ID NO:14;
(n) methylation of H2B at an arginine residue corresponding to the arginine residue at position 99 of SEQ ID NO:14;
(o) methylation of H2B at a lysine residue corresponding to the lysine residue at position 5, 23 or 43 of SEQ ID NO:14;
(p) acetylation of H2B at a lysine residue corresponding to the lysine residue at position 5, 12, 15, 20, 24, 85, 108, 116 or 120 of SEQ ID NO:14;
(q) phosphorylation of H2B at a serine residue corresponding to the serine residue at position 14, 32 or 36 of SEQ ID NO:14;
(r) ubiquitination of H2B at a lysine residue corresponding to the lysine residue at position 120 of SEQ ID NO:14;
(s) phosphorylation of H2A.X at a serine residue corresponding to the serine residue at position 1 or 139 of SEQ ID NO:15;
(t) phosphorylation of H2A.X at a threonine residue corresponding to the threonine residue at position 136 of SEQ ID NO:15;
(u) ubiquitination of H2A.X at a lysine residue corresponding to the lysine residue at position 119 of SEQ ID NO:15;
(v) acetylation of H2A.X at a lysine residue corresponding to the lysine residue at position 5 or 9 of SEQ ID NO:15;
(w) methylation of H3.3 at an arginine residue corresponding to the arginine residue at position 2, 17 or 26 of SEQ ID NO: 16;
(x) methylation of H3.3 at a lysine residue corresponding to the lysine residue at position 4, 9, 14, 18, 27, 36, 37 or 79 of SEQ ID NO: 16;
(y) acetylation of H3.3 at a lysine residue corresponding to the lysine residue at position 9, 14, 18, 23 or 27 of SEQ ID NO:16;
(z) phosphorylation of H3.3 at a serine residue corresponding to the serine residue at position 10 or 28 of SEQ ID NO:16; and
(aa) phosphorylation of H3.3 at a threonine residue corresponding to the threonine residue at position 11 of SEQ ID NO:16.

18. The method according to claim 4 wherein the biological fluid sample is a blood, plasma, serum lymph, urine, synovial fluid, spinal fluid, saliva, or mucous sample.

19. The method according to claim 4 wherein said first antibody or said second antibody is immobilised.

20. The method according to claim 19 wherein the non-immobilised antibody of said first antibody and second antibody comprises a detectable label.

* * * * *